United States Patent [19]

Mueller et al.

[11] Patent Number: 4,548,990
[45] Date of Patent: Oct. 22, 1985

[54] CROSSLINKED, POROUS POLYMERS FOR CONTROLLED DRUG DELIVERY

[75] Inventors: Karl F. Mueller, New York; Sonia J. Heiber, Bedford Hills, both of N.Y.

[73] Assignee: Ciba-Geigy Corporation, Ardsley, N.Y.

[21] Appl. No.: 523,236

[22] Filed: Aug. 15, 1983

[51] Int. Cl.$^4$ .................. C08L 75/00; C08G 73/12; A61K 9/22
[52] U.S. Cl. ..................... 525/123; 526/262; 526/264; 526/320; 526/332; 526/333; 526/334; 424/19; 424/80; 424/81
[58] Field of Search ............... 424/80, 81, 19; 525/123

[56] References Cited

U.S. PATENT DOCUMENTS

| | | |
|---|---|---|
| 3,390,050 | 6/1968 | Speiser . |
| 3,432,592 | 3/1969 | Speiser . |
| 3,538,214 | 11/1970 | Polli et al. . |
| 3,732,865 | 5/1973 | Higuchi et al. . |
| 4,136,250 | 1/1979 | Mueller et al. . |
| 4,184,020 | 1/1980 | Lim et al. . |
| 4,192,827 | 3/1980 | Mueller et al. . |
| 4,224,427 | 9/1980 | Mueller et al. . |
| 4,244,941 | 1/1981 | Lerk . |
| 4,267,138 | 5/1981 | Dobo et al. . |

Primary Examiner—Donald B. Moyer
Assistant Examiner—C. Joseph Faraci
Attorney, Agent, or Firm—Luther A. R. Hall

[57] ABSTRACT

A controlled-release, drug-delivery composition which comprises (A) a crosslinked copolymer, capable of swelling in ethanol to give a swollen copolymer containing at least 40% by weight of ethanol, and capable of swelling in water to give a swollen copolymer containing no more than 20% by weight of water, where the swelling ratio (% ethanol: % water) is 2:1 to 22:1, which comprises the copolymerization product of (a) 50 to 99% by weight of said copolymer of a water-insoluble monoolefinic monomer or (a) with 0 to 45% by weight of total monomers of a water-soluble monoolefinic monomer, with (b) 50 to 1% by weight, but not more than 20 mol % of a divinyl or polyvinyl crosslinking agent; and (B) an effective amount of a pharmaceutical medicament is useful for the controlled and prolonged release of drugs when taken orally.

15 Claims, No Drawings

CROSSLINKED, POROUS POLYMERS FOR CONTROLLED DRUG DELIVERY

BACKGROUND OF THE INVENTION

In the pharmaceutical industry much work has been devoted during recent years to improving the effectiveness, safety and practicality of orally administered drugs. This invention is specifically directed toward the goal of prolonging the release of an orally taken drug over a period of several hours. Such a prolonged release has the following advantages: peak blood levels of the drug, which sometimes represent toxic levels, are avoided since not all the drug is released into the stomach at the same time; secondly, drug concentrations in the blood are maintained for a longer time within the therapeutic range, thereby increasing the overall effectiveness of the drug and reducing the overall dose-size necessary for treatment; thirdly, drugs which would have to be taken in conventional form several times daily for the treatment of chronic diseases, can be administered in once- or twice-a-day dose forms, which are safer and more convenient for the patient.

Conventional dose forms of orally taken drugs are tablets or pills in which the drug is compounded with a water soluble gum or polysaccharide which quickly dissolves or disintegrates in the stomach. An extension of this technology are tablet coatings and multiple coatings around tablets which retard the disintegration and dissolution speed. Material and synthetic polymers with different molecular weight and water solubilities are used for this purpose. U.S. Pat. No. 3,432,592 describes an advanced formulation of this sort, which consists of injection-molded water soluble polymers, like poly(vinyl alcohol), containing drugs dispersed therein.

None of these methods work satisfactorily. Tablet disintegration is fast and poorly reproducible since it is to a large degree a function of physical motion in the stomach. Therefore, polymeric dosage-forms were developed in which the drug-release is diffusion-controlled, independent of physical variables other than polymer compositions and morphology. In these dosage forms the polymer is passed through the body without degradation.

Examples of such a monolithic dose form with uniform drug concentrations are described in Australian Pat. No. 16202, and in U.S. Pat. No. 3,390,050, wherein hydrophilic polymer beads are synthesized in the presence of a drug. U.S. Pat. No. 4,267,138 describes an oral dose form in which the release of an active ingredient is controlled by a coating surrounding drug containing particles, which are compressed into tablets. The coatings are complicated mixtures of plasticized synthetic polymers and water.

U.S. Pat. No. 3,538,214 also describes coated tablets, in which the coating acts as a porous membrane, letting water pass through to dissolve the enclosed drug, which in turn diffuses to the outside. Porous membranes are obtained and their porosity is controlled by addition of auxiliary, water-soluble substances to the coating material which are loaded out prior to drug-diffusion. Similar membrane enclosed oral dose forms are described in U.S. Pat. Nos. 3,854,480, 3,993,072 and 4,244,941.

When used in combination with water-soluble drugs, the above mentioned membrane devices all have the drawback of uncontrollable expansions and breaking due to osmotic pressure build up. This problem was overcome by applying the osmotic pump principle, as described in J. Pharm. Sci. 64, 1981 (1975). This consists of a semipermeable membrane, which lets only water diffuse into the tablet to dissolve the drug, which in turn is pumped out through a pinhole in the membrane. Although this method works well with moderately soluble drugs, it is less applicable to highly water-soluble ingredients because the osmotic pressure quickly become too high as the drug-reservoir is dissolved. As in all membrane devices, constant release is achieved only as long as an undissolved drug reservoir is present in the core. Another disadvantage of the osmotic pump is the high level drug concentration existing at the exit hole which can lead to irritation of the stomach wall.

The above mentioned monolithic polymer-drug compositions of U.S. Pat. No. 3,390,050 and Australian Pat. No. 16202 do not have these disadvantages. In U.S. Pat. No. 3,390,050 no final polymer purification can be carried out since the drug is incorporated during synthesis.

Australian Pat. No. 16202 describes the use of a water swellable poly(2-hydroxyethyl methacrylate) or copolymers of 2-hydroxyethyl methacrylate to imbibe drugs from an aqueous solution. The dried polymer-drug composite forms a controlled oral release device. A similar approach, but using water-swellable polymers (hydrogels) which are themselves two-phase polymers and which exhibit a much wider range of swelling in water and organic solvents is described in U.S. Pat Nos. 4,192,827 and 4,136,250. Although in all these polymers certain drugs can be imibibed in sufficient amounts to make the manufacture of practical dosage forms possible, their relatively high degree of swelling in water (30 to 80%) is concomitantly accompanied by a relatively low degree of swelling in organic solvents. Typically the ratio of % swelling in ethanol to % swelling in water for these hydrogels lies in the range of 1/1 to 2/1.

Furthermore, in these hydrogel drug-carriers, as a high degree of swelling in water is accompanied by a high degree of swelling in organic solvents, concomitantly a low degree of swelling in water is accompanied by a similarly low degree of swelling in organic liquids like ethanol. This limited swelling ability of the hydrogels limits the amount of drug which can be imbibed into them from a drug solution, be it aqueous or organic in nature. If the polymer swells to a larger degree in a suitable organic solvent than in water, then higher drug-loadings can be achieved by loading from, for instance, ethanol/drug solutions than from aqueous solutions provided the drug is soluble in ethanol. The use of organic solvents to imbibe hydrogels with a drug for later release has also been described in U.S. Pat. No. 4,192,827.

SUMMARY AND OBJECTS OF THE INVENTION

It is an object of this invention to produce a controlled-release, drug delivery composition comprising an effective amount of a pharmaceutical medicament in a polymer substrate which can swell in polar organic solvents to a much greater degree than conventional polymers used for drug-delivery and which therefore can be imbibed with active ingredients to a correspondingly high concentration while at the same time exhibiting only a moderate degree of swelling in water.

The ability of a polymer to absorb a large amount of water has always been considered a necessity for a polymeric orally used drug-delivery matrix. Hydrogels have therefore been the only materials previously used for this purpose. Drug diffusion through hydrophobic polymers is normally too slow to be of practical use in an oral drug-delivery. It is consistent with this explanation that hydrophobic polymer-medicament compositions have been used only as body implants where drug delivery over several weeks or even months is desired and where the overall dose size is very low, as is the case, for instance, with steroids.

It has now very unexpectedly been discovered that polymers can be synthesized in aqueous suspension or in bulk which can swell in organic solvents such as ethanol to a much greater extent than conventional hydrogels, being capable of absorbing from 40 to 90% by weight of ethanol and typically showing a ratio of swelling (% ethanol: % water) of 3:1 to 9:1. Therefore these beads can be loaded from a drug solution in an organic solvent with a soluble drug to correspondingly much higher drug levels than can convention hydrogel-type polymeric drug-carriers. At the same time it has been discovered that even if the amount of water absorbed by the novel polymers is lower than that of conventional hydrogels, namely lying in the range of 2-20% by weight of water, they still satisfy the requirement of releasing imbibed drugs completely within one to six hours.

The novel controlled-release, drug-delivery compositions of the present invention comprise:

(A) a crosslinked copolymer, capable of swelling in ethanol to give a swollen copolymer containing at least 40% by weight of ethanol, and capable of swelling in water to give a swollen copolymer containing no more than 20% by weight of water, where the swelling ratio (% ethanol: % water) is 2:1 to 22:1, and (B) an effective amount of a pharmaceutical medicament.

The drug-containing, copolymer beads are synthesized by free-radical initiated polymerization of the above-mentioned monomers in aqueous suspension, preferably in the presence of 1-50% by weight of an inert diluent, followed by imbibing the washed and dried polymer with a drug or other active ingredient dissolved in an organic solvent which solvent is subsequently removed by heating or in vacuo.

It is a further object of this invention to prepare copolymers which exhibit unexpectedly high degrees of swelling in organic solvents while their degree of swelling in water is only moderate or low. Therefore, they can imbibe large amounts of medicaments or other active ingredients from organic solutions, yet are ideally suited for the controlled and prolonged release of such active ingredients into an aqueous environment as an oral dosage in form of beads.

DESCRIPTION OF THE INVENTION

The instant invention pertains to a controlled-release, drug-delivery composition which comprises:

(A) a crosslinked copolymer, capable of swelling in ethanol to give a swollen copolymer containing at least 40% by weight of ethanol, and capable of swelling in water to give a swollen copolymer containing no more than 20% by weight of water, where the swelling ratio (% ethanol: % water) is 2:1 to 22:1, which copolymer is the copolymerization product of (a) 50 to 99% by weight of said copolymer of (aa) a water-insoluble monoolefinic monomer, or mixture of said monomers, or a water-insoluble monoolefinic monomer, or mixture of said monomers with 0 to 45% by weight of total monomers of (bb) a water-soluble monoolefinic monomer, or mixture of said water-soluble monomers, with (b) 50 to 1% by weight of said copolymer of a divinyl or polyvinyl crosslinking agent having a molecular weight of 100 to 10,000, but where (b) is not more than 20 mol % of component (a), and (B) an effective amount of a pharmaceutical medicament.

Preferably the crosslinked copolymer has a swelling ratio (% ethanol: % water) of 3:1 to 15:1; most preferably 4:1 to 8:1.

In order to assure that the instant copolymers have high swellability in ethanol coupled with moderate swellability in water it is preferable that at least a third by weight of the water-insoluble monomer of component (a) is a monomer with an alkyl group of 4 to 21 carbon atoms.

A preferred embodiment of the instant invention is a composition wherein the copolymer (A) is the copolymerization product of 75-98% by weight of component (a) and 25-2% by weight of component (b).

Another preferred embodiment of the instant invention is a composition wherein component (a) comprises 70-95% by weight of water-insoluble monomer (aa) and 30-5% by weight of water-soluble monomer (bb).

A particularly preferred embodiment is a composition wherein component (a) is 75-0% by weight of methyl acrylate, methyl methacrylate or mixture thereof, and 25-100% by weight of a $C_4$–$C_{10}$ alkyl acrylate or methacrylate, or mixture thereof.

(a) The Vinyl Monomers

The monomers used to prepare the crosslinked copolymers of the present invention can conveniently be divided into water-insoluble (aa) and water-soluble (bb) monomers. The water-insoluble comonomers include: the acrylic- and methacrylic esters and amides of monohydric linear or branched alcohols with from 1 to 2 carbon atoms, and which alcohols may be aliphatic, cycloaliphatic, or aromatic in nature. Examples are: methyl -, ethyl-, propyl-, iso-propyl-, n-, iso-, and tertiary butyl-, hexyl-, pentyl-, 2-ethylhexyl-, n-octyl-, 1,1,3,3-trimethylbutyl, decyl-, tridecyl-, hexadecyl-, stearyl-, cyclohexyl-, isobornyl-, dicyclopentadienyl-, menthyl-, dicyclopentadienylethyl-; phenyl-, benzyl-, methoxyethyl; ethoxyethyl-, furfuryl-, glycidyl-, acrylate or methacrylate as well as the corresponding amides; and acrylonitrile;

Vinyl esters, such as: vinyl acetate, vinyl propionate, vinyl benzoate.

Vinyl ethers such as: methyl-, propyl-, butyl-, methoxyethyl-vinyl ether. Fumarate, maleate and itaconate di-esters of the monohydric alcohol-residues mentioned above; styrene, α-methylstyrene.

The monomers may be used alone or in combination with each other. It is preferred that at least half of the water-insoluble monomers are monomers containing alkyl groups with at least 4 carbon atoms, such as butyl acrylate or methacrylate; 2-ethylhexyl acrylate or methacrylate; n-octyl acrylate or methacrylate; di-n-butyl fumarate; benzyl methacrylate; vinyl butyrate; 1,1,3,3-tetramethylbutylacrylamide- and methacrylamide.

Preferred water-insoluble comonomers are methyl methacrylate, n-butyl acrylate, n-butyl methacrylate, 2-ethylhexyl acrylate, n-octyl acrylate and n-octyl methacrylate, glycidyl methacrylate and vinyl acetate or mixtures thereof.

Compositions where 10–60% by weight of component (a) is n-butyl acrylate or 2-ethylhexyl acrylate are especially preferred.

The water-soluble monomer, bb, are preferably acrylic and/or methacrylic acid or the water-soluble derivatives thereof, such as hydroxyalkyl esters where alkyl is 2 to 4 carbon atoms, e.g. 2-hydroxyethyl, 3-hydroxypropyl, 2-hydroxypropyl or 2,3-dihydroxypropyl esters; also ethoxylated and polyethoxylated hydroxyalkyl esters such as esters of alcohols of the formula

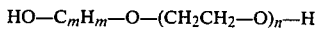

where:
m represents 2 to 5 and
n represents 1 to 20, or esters of analogous alcohols, wherein a part of the ethylene oxide units is replaced by propylene oxide units. Also suitable are 3-(dimethylamino)-2-hydroxypropyl esters and amides. Another class of suitable derivatives of such acids are their water-soluble amides, such as unsubstituted amides and amides substituted by lower hydroxyalkyl, lower oxaalkyl or lower dialkylaminoalkyl groups where alkyl is 2 to 4 carbon atoms such as N-(hydroxymethyl)-acrylamide and -methacrylamide. N-(3-hydropropyl)acrylamide, N-(2-hydroxyethyl)methacrylamide and N-[1,1-dimethyl-2-(hydroxymethyl)-3-oxabutyl]acrylamide; water soluble hydrazine derivatives, such as dimethyl-2-hydroxypropylamine methacrylimide and the corresponding derivatives of acrylic acid.

Also useful, in combination with comonomers, are the lower hydroxyalkyl maleic esters and vinyl ethers where alkyl is 2 to 4 carbon atoms, for instance, di-(hydroxyalkyl)maleates, such as di(2-hydroxyethyl)maleate, and ethoxylated hydroxyalkyl maleates, hydroxyalkyl monomaleates, such as 2-hydroxyethyl monomaleate and alkoxylated hydroxyalkyl monomaleate together with vinyl ethers, vinyl esters, styrene or generally any monomer which will easily copolymerize with maleates or fumarates; hydroxyalkyl vinyl ethers, such as 2-hydroxyethyl vinyl ether, 4-hydroxybutyl vinyl ether, together with maleates, fumarates, or generally all monomers which will easily copolymerize with vinyl ethers.

Other water-soluble comonomers useful in this invention are: alkyl ethers of polyethoxylate hydroxyalkylesters of acrylic and methacrylic acid, such as esters of alcohols of the formula

where
m=2 to 5 and,
n=4 to 20.

Dialkylaminoalkyl esters and amides, such as 2-(dimethylamino)ethyl or 2-(diethylamino)ethyl acrylate and methacrylate, as well as the corresponding amides; amides substituted by lower oxa-alkyl or lower dialkylamino alkyl groups, such as N-(1,1-dimethyl-3-oxabutyl)acrylamide; water-soluble hydrazine derivatives, such as trialkylamine methacrylimide, e.g., triethylamine-methacrylimide and the corresponding derivatives of acrylic acid. Monoolefinic sulfonic acids and their salts, such as sodium ethylene sulfonate, sodium styrene sulfonate and 2-acrylamido-2-methylpropanesulfonic acid; or monoolefinic derivatives of heterocyclic nitrogen-containing monomers, such as N-vinylpyrrole, N-vinylsuccinimide, 1-vinyl-2-pyrrolidone, 1-vinylimidazole, 1-vinylindole, 2-vinylimidazole 4(5)-vinylimidazole, 2-vinyl-1-methylimidazole, 5-vinylpyrazoline, 3-methyl-5-isopropenylpyrazole, 5-methylenehydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinylyridine, 5-vinyl-2-methylpyridine, 2-vinylpyridine-1-oxide, 3-isopropenylpyridine, 2- and 4-vinylpiperidine, 2- and 4-vinylquinoline, 2,4-dimethyl-6-vinyl-a-triazine and 4-acrylylmorpholine.

Preferred among the water-soluble monomers are N-vinyl-2-pyrrolidone, 2-vinylpyridine, 4-vinylpyridine, 2-(dimethylamino)ethyl methacrylate, N-methacrylamide, N,N-dimethylacrylamide, acrylic acid and methacrylic acid or mixtures thereof.

Most preferred water-soluble comonomers are: 2-hydroxyethyl acrylate and methacrylate, acrylic- and methacrylic acid; 2-dimethylaminoethyl methacrylate; N,N-dimethylacrylamide and N-vinyl-2-pyrrolidone.

(b) The Divinyl or Polyvinyl Crosslinking Agent

The insoluble di- or polyacrylates and methacrylates of diols and polyols, such as: linear or branched aliphatic diols such as ethylene glycol, 1,2-propylene glycol, 1,6-hexanediol, 1,4-butanediol, 1,4-butenediol, 1,4-butynediol; diethylene glycol; dipropylene glycol, dipentylene glycol; polyethylene oxide glycol; polypropylene oxide-glycol, polytetramethyleneoxide glycol; poly-(ethylene oxide-co-propylene-oxide) glycol; thiodiethylene glycol; the reaction-product of a diisocyanate (aliphatic, cycloaliphatic and aromatic) with twice the equivalent amount of hydroxyalkyl acrylates or methacrylates; the reaction products of isocyanate terminated prepolymers derived from poly-ester diols, poly-ether diols or polysiloxane diols as shown in the art of polyurethane technology, with from 500–10,000 MW, with twice the equivalent amount of hydroxyalkyl methacrylates. Other such di- and polyvinyl-crosslinking agents, including divinyl ethers and di-allyl compounds are described in U.S. Pat. No. 4,192,827, useful polysiloxane-di and polyvinyl compounds are described in U.S. Pat. No. 4,136,250. The appropriate portions of said patents are incorporated herein by reference.

Examples of such crosslinking agents include: trimethylolpropane triacrylate, neopentylglycol diacrylate, pentaerythritol and dipentaerythritol di-, tri-, tetra-, penta-, hexa-acrylates; ethylene glycol and diethylene glycol acrylates, divinyl ether; divinylbenzene; allyl methacrylate; diallyl maleate; diallylamine; divinyl sulfone; triallyl cyanurate.

Such a crosslinking agent is a terminal diolefinic hydrophobic macromer having a molecular weight from about 400 to about 8000, said macromer having the formula

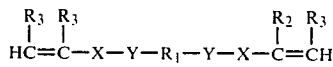

wherein $R_1$ is a chain having a molecular weight from about 200 to about 8000, which is the residue of a poly(-propylene oxide) or poly(tetramethylene oxide) glycol having ether linkages; $R_2$ is hydrogen, methyl or —CH$_2$COOR$_4$, wherein $R_4$ is hydrogen or an alkyl group with up to 10 carbon atoms; $R_3$ is hydrogen or COOR$_4$, with the proviso that at least one of $R_2$ and $R_3$ is hydrogen; X is oxa, —COO—, or —CONR$_5$— is hydrogen or alkyl with up to 5 carbon atoms and Y is a direct bond or the radical —R$_6$—Z$_1$—CO—NH—R$_7$—NH—CO—Z$_2$—, wherein R$_6$ is linked to X and represents branched or linear alkylene with up to 7 carbon atoms; $Z_1$ and $Z_2$ is oxa or NR$_5$ and R$_7$ is the diradical of an aliphatic or aromatic diisocyanate, with the proviso that in case X is oxa, Y is different from a direct bond and $R_2$ and $R_3$ are hydrogen.

Preferably $R_1$ is a poly(propylene oxide) or poly(tetramethylene oxide) chain with a molecular weight of about 600 to about 4,000. Preferably the macromer is a polytetramethyleneoxide glycol with a molecular weight of about 600 to about 4000,, endcapped with toluene or isophorone diisocyanate and reacted with 2 moles of a hydroxyalkyl acrylate or methacrylate, wherein alkyl has 2 to 4 carbon atoms.

Other preferred crosslinking agents include the $C_2$-$C_6$ alkylene diacrylates or methacrylates, 3-oxapentamethylene diacrylate, 3-oxapentamethylene dimethacrylate and trimethylolpropane triacrylate, or mixtures thereof.

The amount of crosslinking agent can vary from 1 to 50% by weight, but should not contribute more than 20 mol. % of the total monomer mixture. Preferred crosslinking agents are ones with a molecular weight from 500–5,000, containing polyalkylene ether units, especially as described in U.S. Pat. No. 4,192,827.

A particularly preferred embodiment of the instant invention are those compositions where the copolymer (A) is the copolymerization product of 85–99% of component (a) and 15–1% of component (b), where (a) is 15–50% by weight of methyl methacrylate, 15–70% by weight of 2-ethylhexyl acrylate, n-butyl acrylate or n-octyl acrylate, 5–15% by weight of N-vinyl-2-pyrrolidone and 0–25% by weight of 2-hydroxyethyl methacrylate.

The Inert Diluent

The inert diluent present during polymerization can be any organic liquid which will clearly dissolve in the monomer mixture. However, it need not be a solvent for the polymer and can vary in its solvent power for a thermodynamically good solvent for monomers and polymers to a thermodynamically poor solvent for the polymer.

Inert diluents which are thermodynamically good solvents for the monomers, but poor solvents for the copolymer are commonly used in the preparation of macroporous ion-exchange resins which are copolymers of styrene and divinylbenzene. The preparation of macroporous hydrogels according to the same principle is described in DDR 66283 and U.S. Pat. No. 4,184,020. In all cases the objective was to prepare macroporous hydrogels for gel chromatography or gas chromatography, and none have been used in oral drug-delivery applications. This is understandable since due to their high hydrophilicity the release-rate would be impractically fast.

The use of inert diluents which are thermodynamically good solvents for both the monomers and the resulting copolymers, results in microporous polymers of increased distances between crosslinks (expanded gel structure) comparable to the microporous, homogeneous structure of polymers prepared in absence of such diluents.

A preferred embodiment of the instant invention pertains to compositions prepared with the use of inert diluents which are good solvents for the monomers and which vary from good to poor in solvent power for the copolymers. Thus copolymer with a selected range of microporous to macroporous structures can be prepared by choosing the diluent used. The structure desired in turn is dictated by the solubility characteristics of the drug to be imbibed as well as its dose size.

If the diluent is a good solvent for the polymer, the product is obtained with a network structure which is a microreticular, that is microporous, in nature. This structure is comparable to the one obtained in the absence of solvent when the polymerization is carried out in bulk, but differs from it by a more extended and open network structure as a result of the good solvent present. If, ion the other hand, the diluent is only a solvent for the monomer, but is a non-solvent or precipitant for the polymer, the product is obtained with a macroporous or macroreticular structure which is 2-phase (gaspolymer) in nature. Although the extremes of both possibilities can be well distinguished from each other, intermediate grades of micro- and macroreticular polymers form a continuum between them.

The solvent power and the solubility parameter of the diluent are commonly a function of its chemical nature, like the degree of hydrogen bonding, polar- and nonpolar interactions, presence of hetero atoms and, generally, of the degree of similarity of the diluent to the monomer which is used. The effect of phase separation during polymerization in the presence of an inert diluent is enhanced by an increase in crosslink-density. To choose the right diluents and the right amount of crosslinking agent to get a micro- or macroreticular structure is a task easily performed by anyone skilled in the art of polymer chemistry and especially the art of making ion-exchange resins.

Another group of diluents which are very poor solvents for the polymer formed are other polymers. It is well known that two different polymers will essentially not dissolve in each other due to the extremely low heat of mixing. Therefore, while polymeric diluents can dissolve in the monomer mixture, during polymerization phase-separation between both polymers occurs. After extraction if the inert polymeric diluent, a product is obtained with an extended network structure which is likely to be more macroreticular than microreticular in nature. Such polymeric diluents, like poly-alkylene ether glycols or polyesters are especially preferred in the context of this invention.

Useful low molecular weight diluents are: ester, such as ethyl acetate; butyl cellosolve acetate; butyl acetate; isobutyl acetate; methyl cellosolve acetates; ethers, such as methyl phenyl ether; tetrahydrofuran; alcohols, such as ethanol; isopropanol; n-,,iso- and tert-butanol; lauryl alcohol; octanol; decanol; dodecanol; butyl cellosole; ethyl cellosolve; butyl alcohol; cyclohexanol. Ketones, such as methyl ethyl ketone; methyl iso-butyl ketone; amides, such as dimethylformamide; formamide; acetamide; dimethylacetamide. Dimethyl sulfoxide. Sulfolane. N-methyl-2-pyrrolidone. Also useful are hydrocarbons such as hexane, heptane, cyclohexane or halogenated hydrocarbons like tetrachloroethylene, trichloroethane or trichloroethylene.

Preferred inert diluents are polyalkylene ether glycols, such as polyethylene oxide glycol, polypropylene oxide glycol and poly-n-butyleneoxide glycol, and block-copolymers thereof, octanol, decanol, dodecanol, heptane, or isobutyl acetate.

The Active Ingredient (Drug)

Any of the drugs used to treat the body, both topical and systemic, can be incorporated as the active agent in the copolymeric carrier of this invention. "Drug" is used herein in its broadest sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug. The desired therapeutic effect, and the time span for which it takes the drug to be released. Since a variety of carriers in a variety of sizes and shapes are intended to provide complete dosage regimes for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided. For example, anabolics, e.g. methandrostenolone; analgesics, e.g. acetylsalicyclic acid, phenylbutazone or methadone; androgens, e.g. methyltestosterone; antibiotics, e.g. rifampin; antidepressants, e.g. imipramine or maprotiline; antidiabetics, e.g. phenformin; anticonvulsives, e.g. cabamazepine; antihistamines, e.g. tripelennamine; antihypertensives, e.g. hydralazine; antiinfectives, e.g. trimethoprim; antiparasitics, e.g. nifurimox; antiparkinson agents, e.g. levodopa; antiphlogistics, e.g. naproxen; antitussives, e.g. benzonstate; appetite depressants, e.g. mazindol; bronchodilators, e.g. fenoterol; coronary dilators, e.g. fenalcomine; corticoids, e.g. dexamethasone; cytostatics, e.g. floxuridine; diuretics, e.g. hydrochlorothiazide; hypnotics, e.g. glutethimide; neuroleptics, e.g. reserpine or thioridazine; psycho-analeptics, e.g. methylpenidate; tranquilizers, e.g. diazepam; uricosutics, e.g. sulfinpyrazone; vasodilators, e.g. isoproterenol.

Among the most preferred drugs are oxprenolol. HCl (TRASICOR) diclofenac-sodium (VOLTRAREN), baclofen (LIORESAL) metropolol.HCl (LOPRESSOR), beta blockers, such as oxprenolol and propanolol; calcium channel blockers, such as Nifedipine and Verapamil.

Synthesis of the Copolymer

The copolymers of this invention are synthesized by free-radical initiated polymerization, using either redox-catalysts, peroxy compounds or azo compounds; typical initiators include lauroyl peroxide, tert.-butyl peroctoate and azo-bisisobutyronitrile. As known to those skilled in the art, many different peroxy- and azo compounds are commercially available and can be used. Free radical polymerization can also be UV-initiated in the presence of commonly used UV-initiators and sensitizers such as benzophenone, benzoin, diethyoxyacetophenone (DEAP) and related compounds. Electron-beam radiation can be used if the polymer are made in form of films, coating or sheets.

The polymers are synthesized in form of beads by suspension polymerization process in an aqueous medium. To reduce the solubility of water-soluble comonomers present, the medium is preferably an inorganic salt solution, usually concentrated sodium chloride solution. As suspending agents can be used either polymeric suspending agents such as poly(vinyl pyrrolidone), poly(vinyl alcohol) or poly(hydroxyethyl cellulose), or inorganic, insoluble salts such as calcium phosphate, calcium oxalate, calcium carbonate, calcium sulfate or magnesium phosphate, or the insoluble hydroxides such as $Mg(OH)_2$, $Al(OH)_3$ or $Ti(OH)_4$. A process which can be used to make the polymers of this invention in form of beads is described in U.S. Pat. No. 4,224,427. After synthesis the polymer beads are thoroughly extracted with ethanol or ethanol/water mixtures or other suitable solvents and dried to constant weight. The polymers of this invention can also be manufactured by bulk polymerization methods in form of sheets, films or shapes.

In form of shapes, rods, films or sheets and coatings the instant copolymer can also be made by casting and thermally or UV-initiated polymerization.

The polymers after synthesis are characterized by their degree of swelling in water and ethanol, by their ability to imbibe an active ingredient and the release of this ingredient into an aqueous environment, as described in detail in the examples.

Preparation of a Drug-Containing Composition

After drying, the polymer beads are imbibed with a chosen active ingredient such as a drug. As solvent for imbibing the drug, any solvent which will (a) dissolve the drug, (b) swell the polymer, and (c) can be quantitatively removed can be used. These are preferably low boiling solvents like methanol or ethanol, methylene chloride, acetone or mixtures of such solvents. Aqueous alcoholic solutions are also suitable. The best choice of solvents will depend on the solubility of the drug and on the desired level of loading. In general, however, it will be seen from the accompanying examples, that for many water-soluble drugs, ethanol is also a good solvent and the high ethanol swelling capability of the polymers of this invention makes high drug-loadings from ethanol solutions possible and preferred.

Especially high loading are obtained with certain drugs when the polymer-synthesis is carried out in presence of an inert diluent.

To load the copolymer with an active ingredient, the copolymer is equilibrated in a solution of said active ingredient in ethanol, methanol or other organic solvent or a mixture of such solvents which may also contain water. Subsequently the solvent is driven off by drying in heat or vacuo.

It has further been discovered that especially high drug-loadings can be achieved if the polymerization is carried out in presence of an inert diluent which results in a final polymer of increased pore size and which copolymer therefore is capable of absorbing even higher amounts of solvent and drug.

Drug loaded compositions, in which the polymer is obtained in the presence of such inert diluents as poly(-propylene glycol), decanol or dodecanol are thus a preferred embodiment of the present invention. Despite high drug loadings, beads treated in this manner show a prolonged and delayed release.

Drug Release

Loading up a polymer bead with enough drug to make a practical dose size is only one requirement for a successful oral dosage form; that the drug be released within a practical time span is another. In many cases it is sufficient advantage over conventional dose-forms to release the drug from a monolithic polymeric matrix since such a system reduces the possibility of drug-abuse. Although the release is not constant, but concentration-dependent, it is slowed down enough to eliminate potential toxic overdose effects.

In case where a more constant release is desired, it has unexpectedly been found that polymer-drug compositions of the present invention in which the polymer contains a major proportion—30 to 100% of all hydrophobic monomers—of monomeric units bearing alkyl groups of 4–21 carbon atoms are especially well suited for carrying out the 'controlled extraction' process described in copending application Ser. No. 484,018. In this process, a thin surface region of the drug-loaded bead is rendered free of drug by extraction with a low boiling solvent like acetone for a precise time period, followed by rapid drying. Why these polymers show this unexpectedly useful behavior is not well understood, but may be due to a phase-inversion of polymer segments on the bead-surface under the influence of a solvent. Drug-loaded polymers having 30–70% of their total hydrophobic monomer composition derived from $C_4$–$C_{21}$ alkyl substituted monomers are thus another especially preferred embodiment of this invention.

It has furthermore been found unexpectedly that use of polymeric inert diluents during the synthesis of the polymer beads of the instant invention gave after extraction beads with a specifically modified network structure which resulted in unexpectedly good drug-release characteristics, especially the elimination of excessive tailing.

The polymers of this invention are exceptionally well suited as drug carriers for an oral dose-form, especially when their gel-structure is expanded by use of an inert diluent during synthesis, and contain at least 25% by weight of residues derived from a monomer which is an alkyl acrylate and/or alkyl methacrylate having 4 to 10 carbon atoms in the alkyl group.

In form of shapes, for instance rods, the polymers of this invention are also useful as implantable drug carriers, since their blood- and tissue compatability is excellent.

In form of films or sheets, the polymers of this invention are useful as drug carriers for transdermal devices or wound treatment and bandages.

In the following examples the degrees of swelling in water or ethanol are expressed as percent of water or of ethanol in the swollen polymer, namely:

DS in water of ethanol (%) =

$$\frac{\text{weight of swollen polymer} - \text{weight of dry polymer}}{\text{weight of swollen polymer}} \times 100$$

Drug concentrations (DC) of drug loaded polymers are likewise expressed in % of drug-loaded polymer.

The swelling ratio for a polymer is defined as the ratio % ethanol:% water.

In the following examples MAC refers to a difunctional crosslinking agent obtained by reaction of 2 mols isophorone diisocyanate with 1 mol poly-n-butyleneoxide diol of 2000 average molecular weight, followed by end-capping with 2 moles 2-hydroxyethyl methacrylate.

The following abbreviations are used:
HEMA: 2-hydroxyethyl methacrylate
NVP: N-vinyl-2-pyrrolidone
MMA: methyl methacrylate
EHA: 2-ethylhexyl acrylate
BA: butyl acrylate
t-OCT: tert.-octylmethacrylamide (=1,1,3,3-tetramethylbutylmethacrylamide)
DMA: dimethylacrylamide
MAC: macromer (B) as prepared in Example 1
GMA: glycidyl methacrylate.

EXAMPLE 1

Synthesis of Polymer Beads by Suspension Polymerization

A smooth wall, 1,000-ml resin flask is equipped with a reflux condenser, nitrogen-inlet tube, thermometer attached to a thermoregulator, baffle and anchor-type stirrer driven by a variable speed motor. A slow flow of nitrogen is maintained through the reaction flask at all times.

To the flask are charged 360 grams of 20% by weight aqueous sodium chloride solution followed by 12.5 grams (0.0615 moles), of magnesium chloride-hexahydrate. The solution is heated slowly to 80° with rapid stirring. To this solution is then added dropwise 123 ml (0.123 moles) of a 1-normal sodium hydroxide solution to form a fine, gelatinous precipitate of magnesium hydroxide in the reaction flask.

After all the sodium hydroxide is added, the stirring speed is reduced to 100 rpm and a mixture of 42 g 2-hydroxyethyl methacrylate, 110 g methyl methacrylate and 24 g N-vinylpyrrolidone and 24 g macromer (b) containing dissolved therein 0.2 gram of tert-butyl peroctoate as a free radical polymerization initiator is added. [The macromer (b) is prepared by dissolving 60 grams (ca. 0.024 moles) of a poly(tetramethylene oxide)-glycol (average molecular weight of 2,000) endcapped with isophorone diisocyanate (=3-isocyanatomethyl-3,5,5-trimethylcyclohexyl isocyanate) in 40 grams (0.31 moles) of 2-hydroxyethyl methacrylate (HEMA) and allowing said mixture to react for 27 hours at room temperature. At the end of this period the disappearance of the terminal isocyanate groups is verified by noting the absence of the characteristic infrared spectral band at 2270 cm$^{-1}$ associated with the —NCO group.]

The reaction mixture is stirred under nitrogen at 100 rpm and at 75° C. for three hours. The temperature is then raised to 100° C. for 1 hour after which time the flask is cooled to room temperature. 10 ml of concentrated hydrochloric acid are then added to dissolve the magnesium hydroxide suspending agent. The reaction mixture is then filtered through fine cheesecloth. The isolated product beads are washed with 2,000 ml of water and soaked overnight in 500 ml of ethanol to extract any residual monomer. The beads are then isolated by filtration through a polyester cloth bag, which is then sewn closed, and dried in a home clothes dryer. Uniform spherical beads are obtained in a yield of 184 g (92.7%) which have an average diameter of 0.98 mm and exhibit a percent swelling in water of 16% and in ethanol of 38%.

The following examples demonstrate the unique swelling properties (high % ethanol/% water ratio; % $H_2O > 1\%$) of the polymers.

EXAMPLES 1–12

Using the procedure of Ex. 1 beads with the following compositions and physical properties were synthesized.

| Ex. No. | Compositions (% by weight) |  |  |  |  |  |  | Cross-Linker (B) MAC % | Bead Size (mm) | % Swelling in |  | Swelling Ratio (%/% % Eth./% $H_2O$ |
|---|---|---|---|---|---|---|---|---|---|---|---|---|
| | Comonomers A |  |  |  |  |  |  | | | | | |
| | Hydrophobe ($A_1$) |  |  |  | Hydrophile ($A_1$) |  |  | | | | | |
| | MMA | BA | EHA | t-OCT | HEMA | NVP | DMA | | | Ethanol | Water | |
| 1 | 55 | — | — | — | 21 | 12 | — | 12 | 0.98 | 38 | 14 | 2.7 |
| 2 | 27.5 | — | 27.5 | — | 21 | 12 | — | 12 | 1.05 | 60 | 11 | 5.5 |
| 3 | 27.5 | — | 27.5 | — | 21 | — | 12 | 12 | 0.96 | 63 | 12 | 5.2 |
| 4 | 27.5 | 27.5 | — | — | 21 | 12 | — | 12 | 1.07 | 58 | 10 | 5.8 |
| 5 | 27.5 | — | — | 27.5 | 21 | — | 12 | 12 | 0.85 | 70 | 9 | 7.8 |
| 6 | 15 | — | 40 | — | 21 | 12 | — | 12 | 1.20 | 50 | 11 | 4.5 |
| 7 | 40 | — | 13 | — | 21 | 12 | — | 12 | 1.04 | 64 | 12 | 5.3 |
| 8 | 35 | — | 35 | — | 8 | — | 10 | 12 | 1.05 | 58 | 3 | 19.9 |
| 9 | 18 | 50 | — | — | 8 | — | 12 | 12 | 1.00 | 62 | 9 | 6.9 |
| 10 | 22 | 40 | — | — | 21 | 5 | — | 12 | 1.12 | 62 | 10 | 6.2 |
| 11 | — | — | — | 55 | 8 | — | 25 | 12 | 1.26 | 71 | 17 | 4.2 |
| 12 | — | — | — | 55 | 21 | 12 | — | 12 | 0.84 | 70 | 12 | 5.8 |

EXAMPLE 13

The procedure of Example 2 is repeated, but instead of methyl methacrylate, 27.5% isobornyl methacrylate is used. Colorless beads are obtained with 0.97 mm average diameter with a degree of swelling of in Ethanol=58%, in water 8% and with the swelling ratio of 7.2.

EXAMPLES 14–15

Following the procedure of Example 1, beads containing 21% HEMA, 12% MAC crosslinking agent and 67% of the listed comonomers are prepared:

| Ex. | Hydrophobic Comonomer (% by weight) | Av. Bead size (mm) | % Swelling in |  | Ethanol: water Swelling Ratio (%/%) |
|---|---|---|---|---|---|
| | | | Ethanol | Water | |
| 14 | cyclohexyl (67) methacrylate | 1.20 | 52 | 8.7 | 6.0 |
| 15 | n-butyl acrylate (67) | 1.00 | 70 | 9.9 | 7.1 |

The following examples show that the polymers obtained with higher alkyl ($C_4$–$C_{10}$)acrylates and methacrylates exhibit superior ethanol swelling properties (high % ethanol/% water ratio).

EXAMPLES 16–28

Following the procedure described in Example 1, copolymer beads are synthesized by polymerizing a mixture containing 21% HEMA, 27% N-vinyl-2-pyrrolidone, 12% macromer B and 40% of hydrophobic methacrylates (=MA) and acrylates (=A) with different ester chain length. The percent swelling in ethanol and in water are determined and a maximum in % ethanol-% water swelling-ratio was found.

| Ex. | Hydrophobic Comonomers | Number of Carbon in Ester Chain | % Swelling in |  | Ethanol: water Swelling Ratio (%/%) |
|---|---|---|---|---|---|
| | | | Ethanol | Water | |
| 16 | methyl-MA | 1 | 51 | 37 | 1.4 |
| 17 | ethyl-MA | 2 | 58 | 38 | 1.5 |
| 18 | n-butyl-MA | 4 | 63 | 35 | 1.8 |
| 19 | 2-ethylhexyl-MA | 8 | 68 | 33 | 2.1 |
| 20 | n-octyl-MA | 8 | 63 | 22 | 2.9 |
| 21 | octadecyl-MA | 10 | 45 | 29 | 1.5 |
| 22 | methyl-A | 1 | 56 | 45 | 1.2 |
| 23 | ethyl-A | 2 | 64 | 38 | 1.7 |
| 24 | n-butyl-A | 4 | 72 | 21 | 3.4 |
| 25 | iso-butyl-A | 4 | 57 | 27 | 2.1 |
| 26 | 2-ethylhexyl-A | 8 | 61 | 24 | 2.5 |
| 27 | n-octyl-A | 8 | 54 | 25 | 2.2 |
| 28 | decyl-A | 10 | 52 | 25 | 2.0 |

The copolymer beads made in Examples 16–28 demonstrate the effect of increasing the length of the alkyl ester group in the acrylate or methacrylate hydrophobic monomers on the ability of the beads to swell in ethanol or water. Since the amount of hydrophilic monomer (48% by weight of total monomers) in the copolymers of each of these examples exceeded the upper allowable amount of hydrophilic monomer in the instant invention, the resulting copolymers accordingly absorbed more water (over 20% by weight in the swollen state) than desired for the copolymers of the instant invention.

Nonetheless, the influence of increasing chain length in the hydrophobic monomer on increasing the swelling ratio of the copolymers in ethanol:water is clearly seen.

The following examples show that the ethanol-swelling properties of polymers containing no hydrophobic comonomer (low % ethanol/% water ratio) are inferior to those of polymers of this invention which contain a hydrophobic comonomer component.

EXAMPLES 29-36

Following the general procedure of Example 1, copolymer beads containing no hydrophobic comonomer are synthesized and their percent swelling in ethanol and water determined. As the table shows, when ethanol swelling is over 50%, % water swelling is also very high and the swelling ratio is low. This is in contrast to the polymers of Examples 1-12.

| Ex. | Composition (% by weight) | | | % Swelling in | | Ethanol: water Swelling Ratio (%/%) |
|---|---|---|---|---|---|---|
| | HEMA | NVP | MAC | Ethanol | Water | |
| 29 | 60 | — | 40 | 34 | 17 | 2.0 |
| 30 | 70 | — | 30 | 38 | 25 | 1.5 |
| 31 | 80 | — | 20 | 40 | 30 | 1.3 |
| 32 | 100 | — | — | 46 | 38 | 1.2 |
| 33 | 70 | 10 | 20 | 51 | 40 | 1.3 |
| 34 | 45 | 35 | 20 | 60 | 46 | 1.3 |
| 35 | 35 | 45 | 20 | 66 | 50 | 1.3 |
| 36 | 10 | 75 | 15 | 79 | 68 | 1.2 |

These examples demonstrate that with conventional hydrogel-compositions, as the % ethanol swelling is increased, % water swelling is increased even more dramatically, resulting in a lowering of swelling-ratio values.

EXAMPLE 37

Following the procedure of Example 1 copolymer beads are synthesized by polymerizing a mixture of 42 g HEMA, 66 g MMA, 66 g EHA, 24 g NVP and 2 g ethylene dimethacrylate (EGDM) instead of the macromeric crosslinking agent MAC. Uniformly spherical beads are obtained with an average diameter of 0.72 mm.

Their composition was:
HEMA: 21%;
NVP: 12%;
MMA: 33%;
EHA: 33%;
EGDM: 1%.

The ethanol swelling is 60%, water swelling 11% and the swelling ratio (% Eth/% water)=5.5.

EXAMPLE 38

Synthesis of Polymer Beads with Expanded Gel-Structure by Polymerization in Presence of Inert Diluents A smooth wall, 1,000-ml resin flask is equipped with a reflux condenser, nitrogen-inlet tube, thermometer attached to a thermoregulator, baffle and anchor-type stirrer driven by a variable speed motor. A slow flow of nitrogen is maintained through the reaction flask at all times.

To the flask are charged 360 grams of a 20% by weight aqueous sodium chloride solution followed by 12.5 grams (0.0615 moles), of magnesium chloride-hexahydrate. The solution is heated slowly to 80° with rapid stirring. To this solution is then added dropwise 123 mol (0.123 moles) of a 1-normal sodium hydroxide solution to form a fine, gelatinous precipitate of magnesium hydroxide in the reaction flask.

After all the sodium hydroxide is added, the stirring speed is reduced to 100 rpm and a mixture of 42 g HEMA, 55 g MMA, 55 g EHA, 24 g NVP, 50 g poly-(oxypropylene) glycol, MW 3600, and 24 g macromer (b) containing dissolved therein 0.2 gram of tert-butyl peroctoate as a free radical polymerization initiator is added. (The macromer (b) is prepared as described in Example 1.)

The reaction mixture is stirred under nitrogen at 100 rpm and a 75° C. for three hours. The temperature is then raised to 100° C. for 1 hour after which time the flask is cooled to room temperature. 10 ml of concentrated hydrochloric acid are then added to dissolve the magnesium hydroxide suspending agent. The reaction mixture is then filtered through the cheesecloth. The isolated product beads are washed with 2,000 ml of water and soaked overnight in 500 ml of ethanol to extract any residual monomer and then extracted in a soxhlet with refluxing ethanol. The beads are then isolated by filtration through a polyester cloth bag, which is then sewn closed, and dried in a home clothes dryer. Uniform spherical beads are obtained in a yield of 177 grams (89%) which an average diameter of 0.74 mm and exhibited a percent swelling in water of 12% and in ethanol of 58%.

EXAMPLES 39-48

Following the procedure of Example 38, beads with expanded gel-structure are prepared using the inert diluents listed below. All polymers contain 21% HEMA, 12% NVP and 12% MAC crosslinking agent.

| Ex. No. | Hydrophobic Comonomers (aa) % | | | Diluent. | Bead Size | | % Swelling in | | Swelling Ratio % EtOH/% H₂O |
|---|---|---|---|---|---|---|---|---|---|
| | MMA | BA | EHA | | % | mm | Ethanol | Water | |
| 38 | 27.5 | — | 27.5 | poly(propylene oxide) glycol MW 3600 | 20 | 0.74 | 58 | 12 | 4.83 |
| 39 | 27.5 | — | 27.5 | poly(propylene oxide) glycol MW 3600 | 40 | 1.10 | 72 | 9 | 8.00 |
| 40 | 27.5 | 27.5 | — | poly(propylene oxide) glycol MW 3600 | 20 | 1.10 | 58 | 11 | 5.27 |
| 41 | 27.5 | — | 27.5 | poly(ethylene oxide) glycol MW 4000 | 20 | 0.83 | 64 | 15 | 4.23 |
| 42 | 27.5 | — | 27.5 | poly(ethylene oxide) glycol | 50 | 1.25 | 71 | 10 | 7.10 |

-continued

| Ex. No. | Hydrophobic Comonomers (aa) % | | | Diluent, | % | Bead Size mm | % Swelling in | | Swelling Ratio % EtOH/% H$_2$O |
|---|---|---|---|---|---|---|---|---|---|
| | MMA | BA | EHA | | | | Ethanol | Water | |
| 43 | 27.5 | — | 27.5 | MW 4000 Dodecanol | 50 | 0.88 | 73 | 10 | 7.30 |
| 44 | 27.5 | — | 27.5 | Poly(tetramethylene oxide)glycol MW 2000 | 40 | 1.05 | 69 | 10 | 6.9 |
| 45 | 27.5 | — | 27.5 | Poly(tetramethylene oxide)glycol MW 2000 | 20 | 1.10 | 71 | 12 | 5.9 |
| 46 | 27.5 | — | 27.5 | PLURONIC-L122 (5000) | 20 | 0.95 | 66 | 10 | 6.6 |
| 47 | 27.5 | — | 27.5 | Butyl carbitol Acetate | 20 | — | 65 | 10 | 6.5 |
| 48 | 27.5 | — | 27.5 | Dodecanol (75%) + poly(propylene glycol) (25%) | 50 | 0.96 | 83 | 6 | 13.6 |

The following examples show the preparation and drug-release of oral drug dosage forms by imbibition of the polymers with drug solutions.

EXAMPLES 49-59

10 g of dry polymer beads prepared according to Example 2 and having an average diameter of 1.1±0.1 mm (−16+18 mesh) are immersed and shaken for 12 hours in a solution of 50 g oxprenolol-HCl in 50 g methanol. The beads are filtered off, rinsed free of drug adhering to the surface with absolute ethanol and dried in vacuo at 50° C. to constant weight (10 hours). The drug content of the beads is determined gravimetrically to be 37.3% oxprenolol.HCl.

5 grams of the loaded beads are stirred in 1 liter of distilled water at 37.5° C. The water is circulated through a UV-spectrophotometer to measure the rate of drug release. 50% of the drug is released within 35 minutes and 90% is released within 120 minutes.

Following the same procedure the following polymer-drug compositions are prepared and release rates measured.

| Ex. | Polymer of Example | Polymer Parts by weight | Drug, | % in Solvent | Solution Parts by weight | Drug Content of Polymer % by weight after loading |
|---|---|---|---|---|---|---|
| 49 | 2 | 1 | oxprenolol.HCl | 50% in methanol | 10 | 37.3 |
| 50 | 8 | 1 | oxprenolol.HCl | 60% in methanol | 1.5 | 44.2 |
| 51 | 9 | 1 | oxprenolol.HCl | 50% in methanol | 25 | 38.3 |
| 52 | 9 | 1 | oxprenolol.HCl | 50% in methanol | 1 | 30.6 |
| 53 | 2 | 1 | diclofenac sod. | 35% in methanol | 1.5 | 30.8 |
| 54 | 2 | 1 | diclofenac sod. | 35% in methanol | 1 | 23.5 |
| 55 | 9 | 1 | diclofenac sod. | 35% in methanol | 1.5 | 39.4 |
| 56 | 10 | 1 | diclofenac sod. | 35% in methanol | 1.5 | 31.5 |
| 57 | 2 | 1 | baclofen | 30% in 75/25 ethanol/H$_2$O | 1.25 | 21.0 |
| 58 | 9 | 1 | baclofen | 30% in 75/25 ethanol/H$_2$O | 1.05 | 17.9 |
| 59 | 11 | 1 | oxprenolol.HCl | 50% in methanol | 2.0 | 51.3 |

In no case is 50% of the imbibed drug released before 30 minutes upon treatment with distilled water at 37.5° C.

EXAMPLES 60-71

Following the procedure of Example 49 and using the conditions described below, the following polymer-drug compositions are prepared with beads synthesized in the presence of inert diluents.

| Ex. No. | Polymer of Example | Diluent* | Mesh size of beads | Polymer Parts by weight | Loading Conditions | | Solution Parts by weight | Drug Content of Polymer % by weight after loading |
|---|---|---|---|---|---|---|---|---|
| | | | | | Drug | % Solvent | | |
| 60 | 39 | PPO | 18 | 1 | oxprenolol.HCl | 50% in methanol | 2 | 50.7 |
| 61 | 39 | PPO | 30 | 1 | diclofenac sod. | 35% in methanol | 3 | 51.4 |
| 62 | 40 | PPO | 18 | 1 | oxprenolol.HCl | 50% in methanol | 2 | 50.8 |
| 63 | 46 | PLUR | 18 | 1 | oxprenolol.HCl | 50% in water | 2 | 43.7 |
| 64 | 45 | PTMO | 18 | 1 | oxprenolol.HCl | 50% in methanol | 2 | 46.9 |
| 65 | 47 | BCAC | 18 | 1 | oxprenolol.HCl | 50% in methanol | 5 | 48.1 |
| 66 | 44 | PTMO | 20 | 1 | carbamazepine | 10% in methanol | 2 | 16.3 |
| 67 | 43 | dodecanol | 18 | 1 | diclofenac-sod. | 35% in methanol | 5 | 62.7 |
| 68 | 39 | PPO | 25 | 1 | " | " | 3 | 51.2 |
| 69 | 39 | PPO | 40 | 1 | " | " | 3 | 49.2 |
| 70 | 39 | PPO | 200 | 1 | Tegritol | 20% in methanol | 3 | 21.8 |
| 71 | 48 | Dodecanol + | 16 | 1 | metopolol.HCl | 50% in methanol | 3 | 45.2 |

-continued

| Ex. No. | Polymer of Example | Diluent* | Mesh size of beads | Polymer Parts by weight | Loading Conditions Drug | % Solvent | Solution Parts by weight | Drug Content of Polymer % by weight after loading |
|---|---|---|---|---|---|---|---|---|
| | | PPO | | | | | | |

*PPO = poly(propylene oxide) glycol MW 3600
PLUR = Pluronic-L122 (5000)
PTMO = poly(tetramethylene oxide) glycol MW 2000
BCAC = butyl carbitol acetate

EXAMPLES 72-78

Following the procedure of Example 38 beads are prepared with the following compositions and their degrees of swelling in ethanol and water determined.

| Ex. No. | Composition, % | | | | | | | Diluent % | | Bead Size (mm) | Swelling in | | Swelling Ratio |
|---|---|---|---|---|---|---|---|---|---|---|---|---|---|
| | MAC | HEMA | NVP | MMA | EHA | GMA | EDGM | DD | PPO | | Ethanol % | Water % | % Eth/% H₂O |
| 72 | 12 | 21 | 12 | 7.5 | 27.5 | — | 20 | 40 | | 0.99 | 46.9 | 8.0 | 5.86 |
| 73 | 12 | 21 | 12 | 7.5 | 27.5 | — | 20 | | 40 | 0.95 | 51.6 | 34.8 | 1.48 |
| 74 | 12 | 21 | 12 | 15 | — | 40 | — | 40 | | 0.57 | 48.6 | 19.7 | 2.47 |
| 75 | — | 21 | 12 | 33 | 33 | — | 1 | 40 | | 0.77 | 73.0 | 9.0 | 8.11 |
| 76 | — | 21 | 12 | 33 | 33 | — | 1 | | 40 | 0.96 | 80.2 | 9.0 | 8.91 |
| 77 | — | 10 | — | 49 | — | 40 | 1 | 40 | | 0.88 | 42.8 | 10.8 | 3.96 |
| 78 | — | 10 | — | 10 | — | 40 | 40 | 40 | | 1.12 | 50.1 | 53.6 | 0.934 |

DD = dodecanol
PPO = polypropyleneoxide-glycol

Of the two diluents, PPO is the poorer solvent for the polymer and gives a macroporous morphology as indicated by the high water-swelling with less short-chain-crosslinking agent (EGDM) (Ex. 73), than does DD (Ex. 72).

The following two examples demonstrate the usefulness of drug loaded beads of the instant invention for carrying out the controlled-extraction process, whereby a much prolonged drug-release can be obtained while still mainstaining a high drug content.

EXAMPLE 79

Two 5-gram samples of drug loaded beads from Example 69 are immersed in water for 10 minutes (Treatment A) and for 20 minutes (Treatment B) followed by rapid freeze drying.

The following table shows the resulting drug loadings and times at which 50% and 90% of the drug are released into a stirred volume (1 liter) of water at 37.5° C., continuously circulating through an UV-spectrophotometer cell.

| Beads of Ex. | Drug | % | Time to Release (hours) | |
|---|---|---|---|---|
| | | | 50% | 90% |
| 69 | diclofenac-sod. | 49.2 | 0.3 | 1.65 |
| After treatment A | | 42.3 | 2.45 | 6.25 |
| After treatment B | | 37.4 | 5.33 | 9.71 |

EXAMPLE 80

5 g of drug loaded beads of Ex. 62 are immersed for 10 min. in acetone, followed by rapid freeze-drying in vacuo. Drug content is determined and drug release rates measured, as described above, with the following results:

| Beads of Ex. | Drug | % | Time to Release (hours) | |
|---|---|---|---|---|
| | | | 50% | 90% |
| 62 | Oxprenolol HCl | 50.8 | 0.2 | 1.68 |
| After treatment | | 46.3 | 1.12 | 3.27 |

The following examples show the superiority of beads prepared in the presence of a polymeric inert diluent over beads prepared with a low mol. weight inert diluent in reducing the tailing effect during drug release.

5 gram samples of beads prepared according to Examples 38, 39 and 43 and loaded according to Examples 49–59 with Oxprenolol-HCl and Diclofenac, are treated by the extraction process of copending Application Ser. No. 484,018. Their drug-release is measured by stirring them in 1 liter distilled water at 37.5° C. and circulating the water through an UV-spectrophotometer cell. As shown in the table, the polymeric diluent polypropylene oxide (PPO) results in 90% release within 9 hours, whereas low moleculas weight dodecanol (DD) leads to excessive tailing.

EXAMPLES 81-84

| Ex. No. | Beads of Ex. | Mesh | Diluent | | Drug and Controlled-Extraction Treatment | Drug Loading % | Time to Release | |
|---|---|---|---|---|---|---|---|---|
| | | | | | | | 50% | 90% |
| | | | | | | | of Loaded Drug (Hours) | |
| 81 | 38 | 18 | 20% | PPO | Oxprenolol.HCl, | 31 | 4.4 | 9.1 |
| 82 | 43 | 18 | 50% | DD | 10 min. acetone wash, then freeze drying | 41 | 2.0 | >20 (tailing) |
| 83 | 39 | 30 | 40% | PPO | Diclofenac | 45 | 3.4 | 8.6 |

| Ex. No. | Beads of Ex. | Mesh | Diluent | Drug and Controlled-Extraction Treatment | Drug Loading % | Time to Release 50% (Hours) | Time to Release 90% (Hours) |
|---|---|---|---|---|---|---|---|
| 84 | 43 | 30 | 50% DD | 10 min. water wash then freeze drying | 51 | 0.7 | >20 (tailing) |

What is claimed is:

1. A controlled-release, drug-delivery carrier composition which comprises
a crosslinked copolymer, capable of swelling in ethanol to give a swollen copolymer containing at least 40% by weight of ethanol, and capable of swelling in water to give a swollen copolymer containing no more than 20% by weight of water, where the % ethanol: % water is 2:1 to 22:1 respectively, which copolymer is the copolymerization product of
(a) 50 to 99% by weight of said copolymer of (aa) a water-insoluble monoolefinic monomer, or mixture of said monomers, or mixture of said monomers with 0 to 45% by weight of total monomers of (bb) a water-soluble monoolefinic monomer, or mixture of said water-soluble monomers, with
(b) 50 to 1% by weight of said copolymer of a divinyl or polyvinyl crosslinking agent having a molecular weight of 100 to 10,000, but where (b) is not more than 20 mol% of component (a).

2. A composition according to claim 1 wherein the swollen copolymer the % ethanol: % water is 3:1 to 15:1 respectively.

3. A composition according to claim 2 wherein the swollen copolymer the % ethanol: % water is 4:1 to 8:1 respectively.

4. A composition according to claim 1 where in the copolymer at least a third by weight of the water-insoluble monomer of component (a) is a monomer with an alkyl group of 4 to 21 carbon atoms.

5. A composition according to claim 1 wherein the copolymer is the copolymerization product of 75–98% by weight of component (a) and 25–2% by weight of component (b).

6. A composition according to claim 1 wherein component (a) comprises 70–95% by weight of water-insoluble monomer (aa) and 30–5% by weight of water-soluble monomer (bb).

7. A composition according to claim 1 wherein component (a) is 75–0% by weight of methyl acrylate, methyl methacrylate or mixture thereof, and 25–100% by weight of a $C_4$–$C_{10}$ alkyl acrylate or methacrylate or mixture thereof.

8. A composition according to claim 1 wherein the water-insoluble monomer of component (a) is methyl methacrylate, n-butyl acrylate, n-butyl methacrylate, 2-ethylhexyl acrylate, n-octyl acrylate, n-octyl methacrylate, glycidyl methacrylate, vinyl acetate or mixtures thereof.

9. A composition according to claim 1 wherein 10–60% by weight of component (a) is n-butyl acrylate or 2-ethylhexyl acrylate.

10. A composition according to claim 1 wherein the water-soluble monomer of component (a) is N-vinyl-2-pyrrolidone, 2-hydroxyethyl acrylate, 2-hydroxyethyl methacrylate, acrylic acid, methacrylic acid, N,N-dimethylacrylamide, 2-dimethylaminoethyl methacrylate or mixtures thereof.

11. A composition according to claim 1 where the crosslinking agent of component (b) is a terminal diolefinic hydrophobic macromer having a molecular weight from about 400 to about 8000, said macromer having the formula $$\begin{array}{cc} R_3\ R_2 & R_2\ R_3 \\ |\ \ | & |\ \ | \\ HC{=}C{-}X{-}Y{-}R_1{-}Y{-}X{-}C{=}CH \end{array}$$

wherein $R_1$ is a chain having a molecular weight from about 200 to about 8000, which is the residue of a poly(propylene oxide) or poly(tetramethylene oxide) glycol having ether linkages; $R_2$ is hydrogen, methyl or $-CH_2COOR_4$, wherein $R_4$ is hydrogen or an alkyl group with up to 10 carbon atoms; $R_3$ is hydrogen or $COOR_4$, with the proviso that at least one of $R_2$ and $R_3$ is hydrogen; X is oxa, $-COO-$, or $-CONR_5-$ is hydrogen or alkyl with up to 5 carbon atoms and Y is a direct bond or the radical $-R_6-Z_1-CO-NH-R_7-NH-CO-Z_2-$, wherein $R_6$ is linked to X and represents branched or linear alkylene with up to 7 carbon atoms; $Z_1$ and $Z_2$ is oxa or $NR_5$ and $R_7$ is the diradical of an aliphatic or aromatic diisocyanate, with the proviso that in case X is oxa, Y is different from a direct bond, and $R_2$ and $R_3$ are hydrogen.

12. A composition according to claim 11 wherein $R_1$ is polypropylene oxide or polytetramethyleneoxide chain with a molecular weight of about 600 to about 4000.

13. A composition according to claim 11 wherein said macromer is a polytetramethyleneoxide glycol with a molecular weight of about 600 to about 4000, end-capped with toluene or isophorone diisocyanate and reacted with 2 moles of a hydroxyalkyl acrylate or methacrylate, wherein alkyl has 2 to 4 carbon atoms.

14. A composition according to claim 1 wherein the crosslinking agent (b) is a $C_2$–$C_6$ alkylene diacrylate, a $C_2$–$C_6$ alkylene dimethacrylate, 3-oxapentamethylene diacrylate, 3-oxapentamethylene dimethacrylate, trimethylolpropane triacrylate or mixtures thereof.

15. A composition according to claim 1 where the copolymer is the copolymerization product of 85–99% of component (a) and 15–1% of component (b), where (a) is 15–50% by weight of methyl methacrylate, 15–70% by weight of 2-ethylhexyl acrylate, n-butyl acrylate or n-octyl acrylate, 5–15% by weight of N-vinyl-2-pyrrolidone and 0–25% by weight of 2-hydroxyethyl methacrylate.

* * * * *